Figure 1:

United States Patent [19]
Watson et al.

[11] Patent Number: 5,244,659
[45] Date of Patent: Sep. 14, 1993

[54] COMPOSITION FOR BIOCONTROL OF FIREWEED

[75] Inventors: Alan K. Watson, Pincourt; Richard S. Winder, Ile Perrot, both of Canada

[73] Assignee: The Royal Institution for the Advancement of Learning (McGill University), Quebec, Canada

[21] Appl. No.: 770,313

[22] Filed: Oct. 3, 1991

Related U.S. Application Data

[62] Division of Ser. No. 475,957, Feb. 6, 1990, abandoned.

[51] Int. Cl.⁵ ............................................. C12N 1/20
[52] U.S. Cl. ................................ 424/93 D; 435/254.1
[58] Field of Search ........................... 424/93; 435/254

[56] References Cited

U.S. PATENT DOCUMENTS

| | | | |
|---|---|---|---|
| 3,849,104 | 11/1974 | Daniel et al. | 71/65 |
| 3,999,973 | 12/1976 | Templeton | 71/79 |
| 4,390,360 | 6/1983 | Walker | 71/79 |
| 4,419,120 | 12/1983 | Walker | 71/79 |
| 4,606,751 | 8/1986 | Van Dyke et al. | 71/79 |
| 4,915,724 | 4/1990 | Watson et al. | 71/65 |

OTHER PUBLICATIONS

Ev pufle Watson et al., Appeal No. 90-0831.
Kaur et al "Studies on Pectolytic Enzymes . . . etc," Indian Phytopathol, 1980 33(2) 333-4 CA96:213917y.
Roy "The Influence of carbon sources . . . etc." Physiol. Micro Org. Symp 1976 (Pub1977) 69-74 CA91:206491m.
Stanbury et al., Principles of Fermentation Technology, 1984 Pergamon Press, Oxford.
Roy, CA91:206991, 1979.
Kaur et al., CA96:213917, 1982.

*Primary Examiner*—Douglas W. Robinson
*Assistant Examiner*—Jean C. Witz
*Attorney, Agent, or Firm*—Cushman, Darby & Cushman

[57] ABSTRACT

The present invention is concerned with a novel bioherbicide and its use to control fireweed, a troublesome competitor of tree seedlings in reforestation areas. More specifically, the invention is concerned with *Colletotrichum dematium* ATCC No. 20981, and its use to control fireweed.

4 Claims, 5 Drawing Sheets

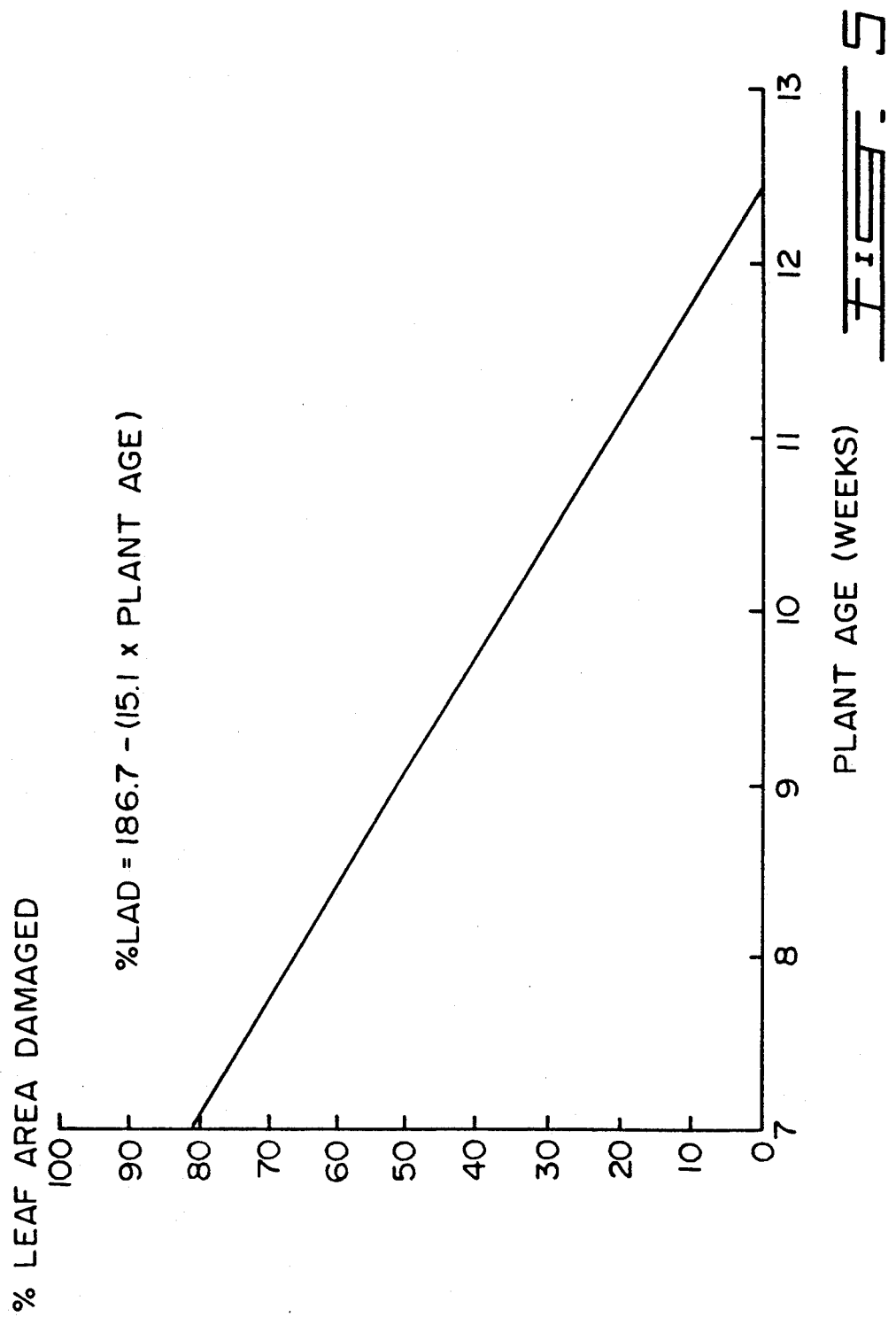

COMPOSITION FOR BIOCONTROL OF FIREWEED

This application is a divisional of application Ser. No. 07/475,957 filed Feb. 6, 1990, now abandoned.

FIELD OF THE INVENTION

The present invention is concerned with the discovery of a novel Colletotrichum species, which is particularly effective as a bioherbicide.

PRIOR ART

Undesirable vegetation is a major problem in reforestation areas, where weeds thrive because of disturbances associated with clearing and site preparation. Epilobium, a genus in the evening primrose family (Onagraceae), is troublesome in many plantation areas. Fireweed (*E. angustifolium* L. subsp. angustifolium) is a species widely distributed in North America and Eurasia. It has minor usefulness as an ornamental flower and as a human food source, but it is a major problem in reforestation areas in Canada. In one example, it infested 17% of reforestation area in the Matapédia region of Québec in 1987. The infestation was as much as 44% in some areas.

Herbicides such as simazine, 6-chloro-N,N'- diethyl-1,3,5-triazine-2,4-diamine; atrazine, 6-chloro-N- ethyl-N'-(2-methylethyl)-1,3,5-triazine-2,4-diamine; EPTC, (S-ethyl dipropylcarbamothioate); glyphosate, N-(phosphonomethyl)glycine; and hexazinone, 3-cyclohexyl-6-(dimethylamino)-1-methyl-1,3,5-triazine-2,4(1H,3H)-dione have been commonly used to control Epilobium spp. in conifer reforestation sites. There are many problems with these control methods. In many areas, there is much public pressure to limit the use of chemical pesticides, which are often perceived as threats to human health and the environment.

Another general problem with forest herbicides is that they are often not very selective, resulting in tree damage or removal of desirable species. There are several specific difficulties with control of fireweed. Epilobium spp. are prolific producers of air-borne seeds and rapidly overtake an area, especially during hardening-off periods when tree seedlings are sensitive to many herbicides. Epilobium can also develop resistance to triazines. The hardy perennial rhizomes of fireweed make control by mechanical cultivation impractical. The inadequacy of present control methods for forest weeds like fireweed has caused many local governments to become concerned with discovering alternative control methods. One alternative under active consideration is the use of biological control agents. Such controls would pose minimal environmental risks and would be relatively inexpensive to develop and register.

The ideal solution to the problem of fireweed competition would be a method of biological control with fungal pathogens. Accordingly, it would be desirable to provide a highly selective virulent pathogen against fireweed.

SUMMARY OF THE INVENTION

In accordance with the present invention, there is provided a novel bioherbicide which is effective in controlling fireweed (*Epilobium angustifolium*) without adversely affecting the growth and yield of desired tree seedlings.

More specifically, the present invention comprises the use of a composition of *Colletotrichum dematium* (*C. dematium*) spores or isolate, in association with an acceptable agricultural carrier, to control fireweed.

It is also an aspect of the present invention to provide a process for controlling fireweed by applying an effective amount of the novel composition of the present invention.

In another aspect, the invention is concerned with providing the novel fungus *Colletotrichum dematium*, which has the identifying characteristics of the culture deposit ATCC No. 20981.

Finally, a preferred composition of the present invention is also disclosed, which further comprises an extract of *Aloe saponaria* Haw.

IN THE DRAWINGS

FIG. 1. Typical effect of $10^9$ conidia/m$^2$ of *C. dematium* isolate #37 applied to 13-week-old fireweed and subsequently exposed to 24 h dew. Example control is on the left and example treatment is on the right.

Figure 2:
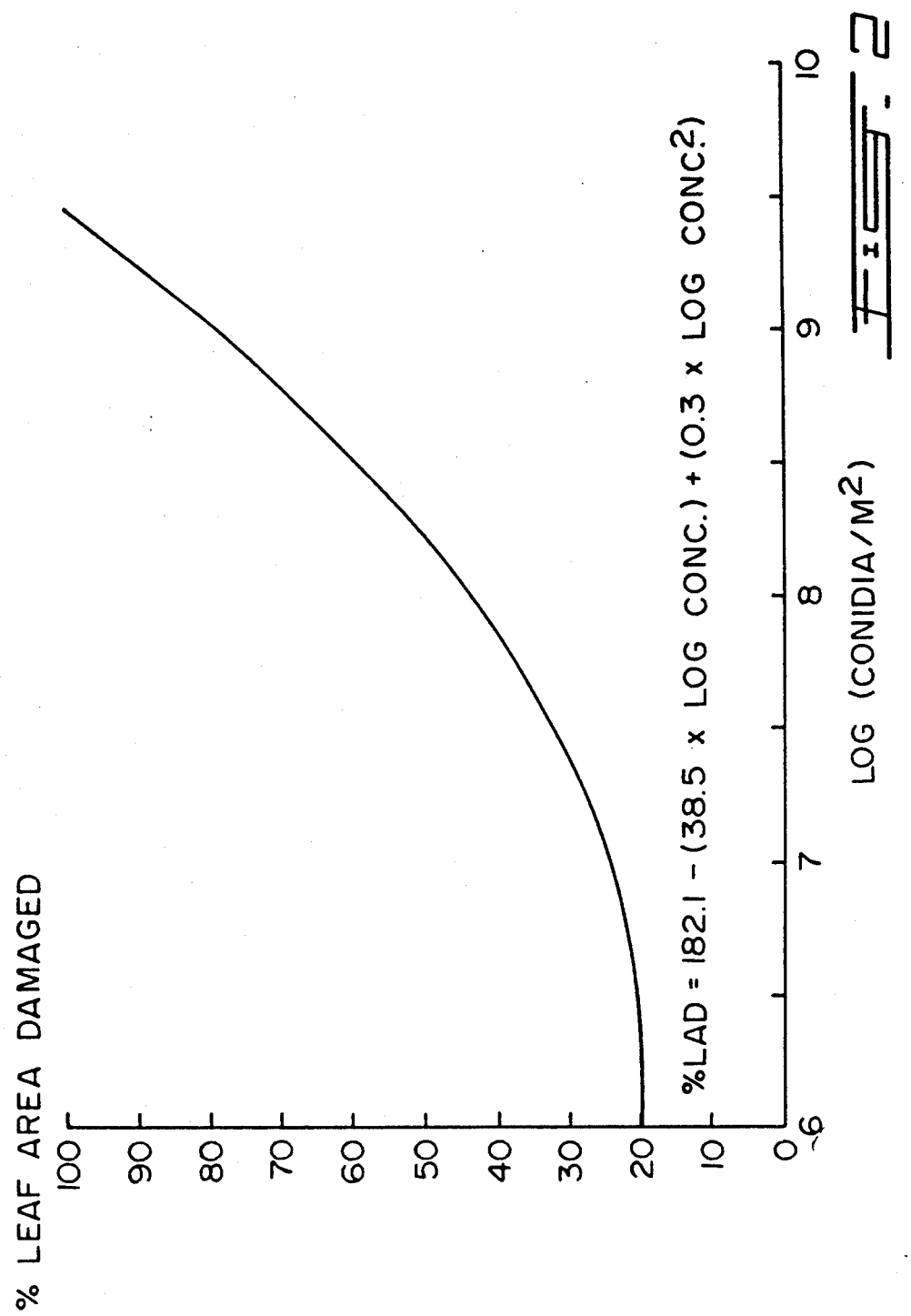

FIG. 2. Effect of inoculum density on damage to fireweed by *C. dematium*, with a dew period of 18 h, a plant age of 7 weeks, and inoculum producing $10^7$ conidia/plate.

Figure 3:
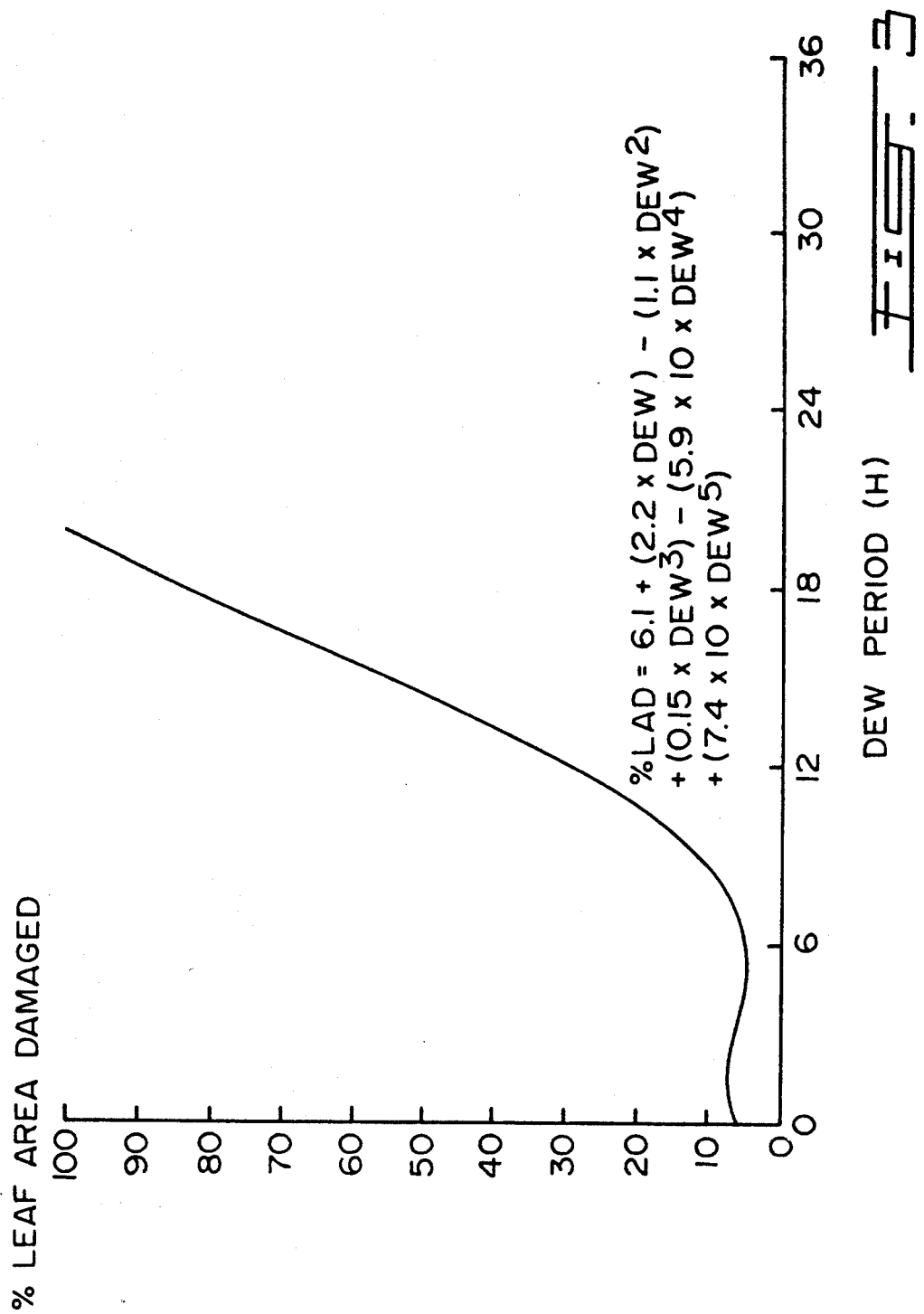

FIG. 3. Effect of dew period on damage to fireweed by *C. dematium*, applied at $10^9$ conidia/m$^2$, with a plant age of 7 weeks and inoculum producing $10^7$ conidia/plate.

Figure 4:
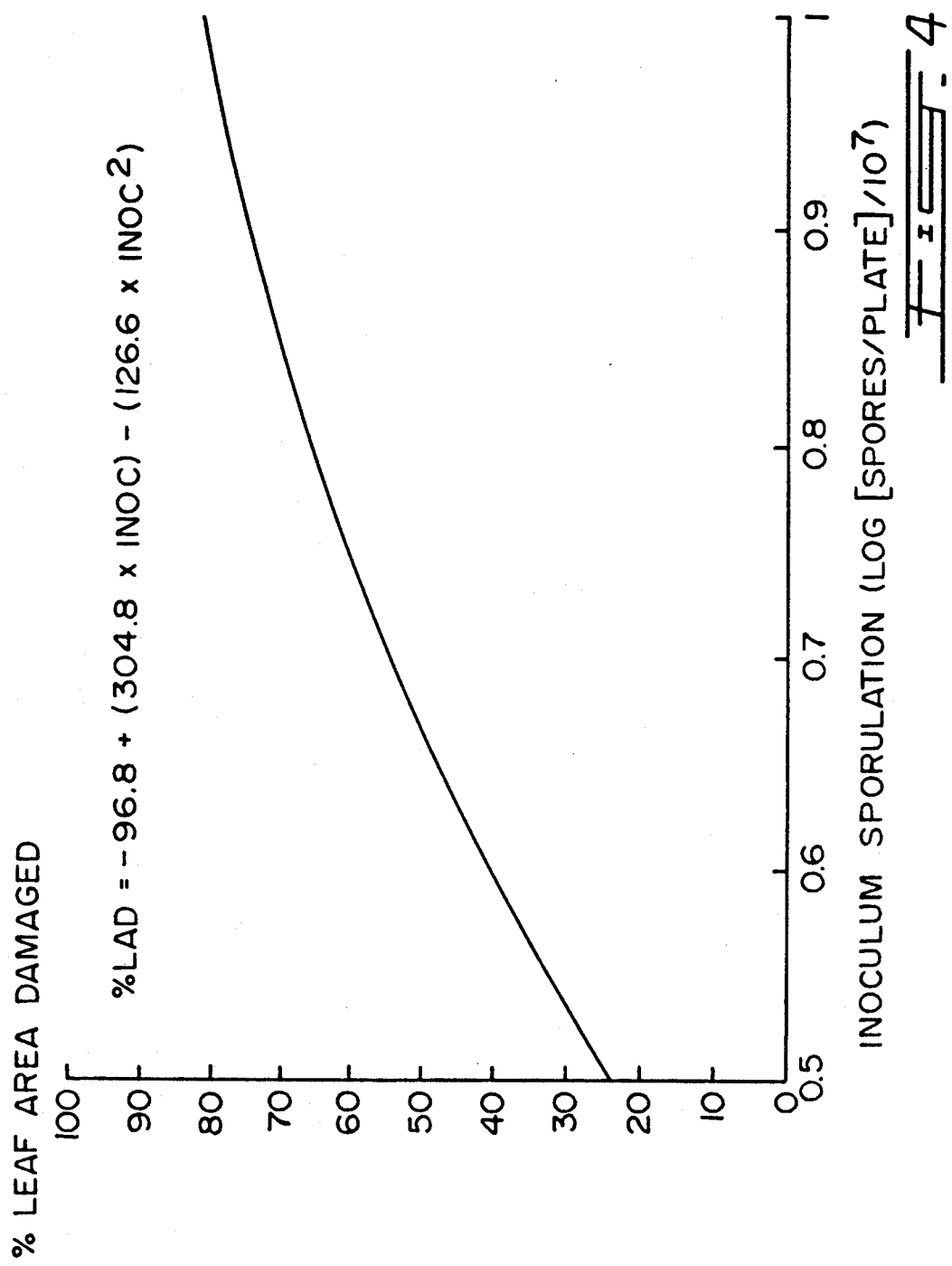

FIG. 4. Effect of sporulation density of inoculum-producing colonies on damage to fireweed by *C. dematium*, applied at $10^9$ conidia/m$^2$, with a dew period of 18 h and a plant age of 7 weeks.

FIG. 5. Effect of plant age on damage to fireweed by *C. dematium*, applied at $10^9$ conidia/m$^2$, with a dew period of 18 h and inoculum producing $10^7$ conidia/plate.

DESCRIPTION OF THE INVENTION

The fungus *Colletotrichum dematium* used in accordance with the present invention has highly desirable bioherbicidal properties. A subculture of *Colletotrichum dematium* has been deposited in the permanent collection of the American Type Culture Collection on Feb. 5, 1990. This deposit was assigned the accession number ATCC No. 20981. This deposit is available to the public upon the grant of a patent disclosing it. The deposit is also available as required by foreign patent laws in countries wherein counterparts of the subject application, or its progeny, are filed. However, it should be understood that the availability of a deposit does not constitute a license to practice the subject invention in derogation of patent rights granted by governmental action.

Collection and Screening

Diseased fireweed was collected in the Rimouski, Matapédia, and Beauce regions of Québec, and in the La Tuque, Lac St. Jean, and Chicoutimi regions of Quebec. Pieces of diseased tissue were immersed in 70% ethanol for 10 seconds, transferred to 1.5% NaClO for 4 min., subsequently rinsed in two changes of sterile water, and placed in petri dishes containing potato dextrose agar (PDA). The cultures were placed 28 cm under 40-W ultraviolet-A fluorescent lights with a 12 h on/off cycle and incubated for 10 days at room temperature. This same method of incubation was used for all subsequent cultures. The resulting colonies from six isolates of each fungus were transferred to PDA slants and incubated for 5 days. About 10 ml of sterile paraffin oil was added to each vial, and the isolates were stored at 5° C.

Plant Propagation and Inoubation

Fireweed seeds were collected in the Beauce region of Quebec in 1988. For screening tests, fireweed was planted in 5 cm-diameter pots containing a commercial potting mix and grown in a growth chamber (12 h photoperiod, 150 uEm$^{-2}$s$^{-1}$, 24/18° C. day/night temperature). For whole plant screening, fireweed was grown in the greenhouse. For pathogenicity and virulence tests, the propagation method was improved. Seeds were germinated in sealed petri dishes containing agar. Germinated seeds were transferred to seed trays containing a 1:1:1 mixture of sand, pasteurized soil, and commercial potting mix. The trays were covered with a plastic lid and placed in growth chambers, where conditions were modified (12 h photoperiod, 300 uEm$^{-2}$s$^{-1}$, 26°-16° C. day/night temperature). Three weeks after planting, the seedlings were individually transferred to 10-cm diameter pots containing a similar soil mixture. Each pot was fertilized weekly with ca. 10 ml of a solution containing ca. 3 g/l of fertilizer.

Screening

Cultures of each fungus to be tested were initiated with transfers of mycelium from storage vials to Petri dishes containing PDA, and incubated for 10 days. Fireweed leaves were placed three per dish in glass Petri dishes containing moist filter paper. Individual inoculum solutions were made by scraping spores and hyphae from one culture into 50 ml of a 0.02% (v/v) surfactant (polyoxyethylene sorbitan mono-oleate) solution. The solutions were individually applied to leaf pieces in respective chambers with a paint brush. The dishes were incubated for 3 days at room temperature, and effects were rated as: 0 (no effect), 1 (slight damage), 2 (up to 10% damage), 3 (up to 50% damage), 4 (up to 100% damage). Fungi receiving a rating of 3 or more were selected for screening on 10-week-old plants. Inoculum was prepared in the same fashion, and applied in a spray chamber using a full cone nozzle 180 kilopascals pressure, 20 cm above the tops of the pots. The final inoculum density was $6 \times 10^6$ conidia/ml of *C. dematium*. The plants were incubated for 18 h in a dew chamber (wall temp. 8° C., water temp. 39° C., air temp. 21° C.) on each of the two nights following incubation. Percent leaf area damaged (% LAD) was evaluated for each leaf after 3 days, and the data were subjected to analysis of variance.

The concentration of the fungus *Colletotrichum dematium* in the composition is from about $10^4$ to $10^6$ spore/ml of carrier. Also, the composition is preferably applied at a rate ratio of from about $10^6$ to $10^9$ spores/ml, and generally applied as a spray.

The following Examples are given to illustrate the present invention, and are not to be construed as limiting its scope.

EXAMPLE 1

Media Comparison

The growth and sporulation of the *C. dematium* fungus tested on whole plants was compared on three different media using a completely randomized experimental design. Media containing fireweed included 40 g of macerated fireweed leaves and stems per liter of medium. Media included PDA, PDA plus fireweed (FPDA), modified V8 juice agar (CZ8), CZ8 with fireweed substituted for corn (CF8), malt extract agar (MEA) and MEA plus fireweed (FMEA). Transfers from PDA storage vials were made to five plates of each medium. The radial growth of each colony was measured after three days, and the data were subjected to analysis of variance with a computer program. The sporulation of each colony was visually assessed after three days using a qualitative scale classifying sporulation as sparse, light, nominal, or heavy in increasing order of magnitude. The best medium for *C. dematium* growth was FMEA, as shown in Table 1.

TABLE 1

A comparison of the growth of *C. dematium* fungus from fireweed on 6 different media.

| Fungus | Growth and sporulation[a] on media[b] | | | | | | LSD[c] |
|---|---|---|---|---|---|---|---|
| | PDA | FPDA | CZ8 | CF8 | MEA | FMEA | |
| Colletotrichum dematium | 5.0 ++ | 8.1 +++ | 5.0 ++ | 7.9 ++ | 5.0 +++ | 8.2 ++++ | 0.6 |

[a]Millimeters of radial growth in three days, with qualitative sporulation ranking directly below in the same column. For sporulation, + = sparse (ca. $10^4$ conidia/plate), ++ = light (ca. $10^5$ conidia/plate), +++ = nominal (ca. $10^6$ conidia/plate), ++++ = heavy (ca. $10^7$ conidia/plate or more).
[b]Media abbreviations are: PDA = potato dextrose agar, FPDA = Fireweed + PDA, CZ8 = cornleaf/V8-juice agar, CF8 = fireweed/V8-juice agar, MEA = malt extract agar, FMEE = fireweed + MEA.
[c]Least significant difference (P < 0.05) between growth means.

EXAMPLE 2

Formulation and Inoculation

A *C. dematium* isolate was selected for further testing on the basis of evident damage and rapid growth. The formulation solutions used with the isolate in further testing consisted of 0.5% (w/v) malt extract, 0.5% (w/v) yeast extract, 0.1M KCl, and 25% extract of *Aloe saoonaria* Haw. *A. saponaria* extract was prepared from the mesophyll scraped from the leaves of plants grown in the greenhouse. The mesophyll was mixed in a blender with the other solution components for 30 s and filtered through a nylon mesh. The pathogen was reisolated from inoculated plants in the previous whole plant comparison and maintained by continuous previous whole plant comparison and maintained by continuous transfer from 10-day-old colonies growing in Petri dishes containing FMEA. For each batch of inoculum, spores were scraped from 20 10-day-old colonies after adding ca. 5 ml distilled water. The resulting spore solution was added to 500 ml of a 0.01M solution of tannic acid (f.w. 1701.18) to attack the conidial matrix proteins. The inoculum was filtered out of solution by vacuum filtration with filter paper after 4 min. The inoculum was scraped from the surface of the filter paper and rinsed with brisk agitation in 500 ml distilled water. The inoculum was refiltered and added to 5 ml of the formulation solution. A hemacytometer was used to estimate the concentration of conidia, and formulation solution was added to achieve the desired concentration. The formulation, which was too viscous for application in the spray chamber, was applied to plants with an atomizer using a 2-second burst at 10 cm above the soil of each pot. Tall plants were turned vertically and exposed to 2-second bursts for each uninocualted portion of the plant. Inoculum density was calculated from the flow rate for 2 seconds applied at a distance of 10 cm.

The application of *C. dematium* conidia with *A. saponaria* extract was consistently lethal to fireweed and very rapid. Mortality was achieved within 24 h (FIG. 1).

EXAMPLE 3

Pathogenicity and taxonomic status

The pathogenicity of *C. dematium* isolate was evaluated on 9 plant species listed in table 1. A completely randomized experimental design was used, with eight replicated treatments and six replicated controls of each kind of plant. An 18 h dew period was used subsequent to inoculation. The % LAD was visually estimated for each plant after 5 days. The reaction in each treatment was rated as susceptible (necrotic lesions), resistant (small flecks), or immune (no symptoms). In resistant and immune plants, the type of defense was observed by noting the presence or absence of spore germination and appressoria formation. If spores did not germinate or appressoria did not form, the defense was categorized as external. If appressoria formed but did not usually damage underlying tissue, the defense was deemed internal.

Fireweed and *E. lanceolatum* Sub. were susceptible to *C. dematium*. *E. glandulosum* Lehmann, *E. coloratum* Biehler, and *Abutilon theophrasti* were resistant. All other plants were immune (Table 2).

To identify the form-species of the isolate, conidial and appressorial dimensions were measured. The widths and lengths of one hundred conidia from an FMEA culture in the medium comparison experiment were observed with a microscope and recorded. Since conidia were falcate, length was measured in terms of the linear distance between ends. The widths and lengths of one hundred appressoria on the leaves of inoculated fireweed from the pathogenicity study below were observed with a microscope and recorded. Width was considered to be the dimension perpendicular to attached germ tubes, or the shortest dimension if no germ tube was visible.

In the microscope observations, conidia of the isolate were falcate, $2.6\pm0.1$ μm (range 2–3 μm) wide and $25.2\pm0.4$ μm (range 20.5–30.00 μm) wide. Apressoria were multilobate, $5.8\pm0.2$ μm (range 6.0–11.0 μm) wide and $8.0\pm0.3$ μm (range 4.0–9.0 μm) long. So far no reports of form species of *C. dematium* pathogens in the Onagraceae with these characteristics have ever been described.

TABLE 2

Pathogenicity of *C. dematium* isolate on several plant species.

| Plant name | Percent leaf area necrotic[a] | Incidence of damage (%) | Plant response[b] |
|---|---|---|---|
| (Onagraceae) | | | |
| *Epilobium* | | | |
| *angustifolium* L.[c] | 88 ± 5 | 100 | S |
| *angustifolium* L.[d] | 80 ± 6 | 100 | S |
| *lanceolatum* Sub. | 7 ± 4 | 100 | S |
| *glandulosum* Lehmann | 8 ± 2 | 87 | ER |
| *coloratum* Biehler | 1 ± 1 | 25 | IR |
| *montainum* L. | 0 | 0 | EI |
| *Oenothera* | | | |
| *perennis* L. | 0 | 0 | II |
| *parviflora* L. | 0 | 0 | II |
| *Circaea* | | | |
| *lutetiana* L. | 0 | 0 | II |
| (Other families) | | | |
| *Abutilon* | | | |
| *theophrasti* Medik | <1 | 0 | R |

[a]There was no necrosis in any control plant.
[b]Abbreviations for resistance types are: S = susceptible, ER = external resistance (conidial) germination and/or appressoria formation frequently inhibited), IR = internal resistance (fungal penetration from apressoria frequently unsuccessful), R = externally and internally resistant, EI = externally immune (like external resistance, but no damage observed), II = internally immune (like internal resistance, but no damage observed).
[c]Subspecies *angustifolium*, collected near Rimouski, Quebec.
[d]Subspecies *angustifolium*, collected near Beauce, Quebec.

EXAMPLE 4

Virulence

The effects of plant age, inoculum density, colony age, colony sporulation and dew period on virulence of the isolate were assessed using a generalized randomized block experimental design. Unless otherwise stated, inoculations were conducted with 7-week-old rosette stage plants, $10^9$ conidida/m$^2$, 10-day-old colonies, and a subsequent dew period of 18 h, with five spatial replications per treatment. In one group of treatments, plants were inoculated at stages. In a second group of treatments, the levels of inoculum density used were 0, $10^6$, $10^7$, $10^8$, and $10^9$ conidia/m$^2$. In the third group of treatments, inoculum was obtained from colony ages of 10, 15, and 20 days. In the fourth group of treatments, the dew period was 0, 6, 12, 18, 24, 30, and 36 h, reduced to four spatial replications per treatment to conserve space in the dew chamber. There were also three replicates in time for all treatments, spaced one week apart. These three temporal replications were treated as blocks corresponding to inoculum batch. For each treatment, sporulation of the inoculum was also noted in terms of the number of conidia per plate. The plants were rated for % LAD 48 h after inoculation, and the resulting data were analyzed with a computer program to form a multiple regression model of treatment effects.

Several factors significantly influenced the virulence of *C. dematium* on fireweed. The multiple regression model for these effects was %LAD $= -71.74 + 238.01\ q - 45.97\ q^2 + 0.06\ p - 38.50\ c + 0.34\ c^2 + 2.24\ d - 1.11\ d^2 + 0.15\ d^3 - (5.99\times10^{-4}\ d^4) + (7.42\times10^{-5}\ d^5) - 9.54\ bp - 24.65\ bc$, where q is the quantity of conidia ($\times 10^7$) conidia per plate, p is the plant age in weeks, c is the log of the number of conidia per m$^2$, and d is the dew period in hours. The effects of inoculum age and serial replication were not significant, indicating that colony maturation of up to 20 days did not affect virulence. There were no significant block effects from serial replication. In the model, damage increased exponentially serial replication. In the model, damage increased exponentially with the log of conidial concentration (FIG. 2). Damage also increased exponentially with dew period; dew periods of 24 h or greater were always lethal for 7-week-old fireweed plants subjected to the highest inoculum dose (FIG. 3). Damage increased in a polynomial fashion with increasing sporulation of the inoculum-producing colonies (FIG. 4). For this organism, colony sporulation may be a general indicator of inoculum potency or virulence. Damage decreased linearly with plant age (FIG. 5). The results for plant age, dew period, and inoculum concentration are similar to those reported for other potential mycoherbicides. These data indicate that the optimum effect of *C. dematium* would be on rosette stage plants with $10^9$ conidia/m$^2$ from colonies containing $10^7$ conidia per plate, and a dew period between 18 to 24 h.

We claim:

1. A composition for agricultural application for controlling fireweed, comprising a solution of an effective amount of an isolate of the fungus *Colletotrichum dematium* having all of the identifying characteristics of the culture deposit No. ATCC 20981, in association with a 25% w/v of an extract of *Aloe saponaria* Haw.

2. A biological *Colletotrichum dematium* characterized as having the property of controlling fireweed having all of the identifying characteristics of culture deposit ATCC 20981.

3. A composition comprising an isolate of the fungus *Colletctrichum dematium* according to claim 2, in association with an agriculturally acceptable carrier.

4. A composition according to claim 2, wherein said isolate is in the spore form at a spore concentration of from about $10^4$ to $10^7$ spores/ml of carrier.

* * * * *